United States Patent [19]

Saito et al.

[11] Patent Number: 5,512,175
[45] Date of Patent: Apr. 30, 1996

[54] ASSEMBLY FOR REMOVING HYDROPHILIC CONTAMINANTS, METHOD OF THE SAME, AND APPARATUS FOR PRODUCING PHENOL

[75] Inventors: Mikio Saito, Sagamihara; Tsuneo Yamaguchi, Kawasaki, both of Japan

[73] Assignee: Wako Industrial Co., Ltd., Tokyo, Japan

[21] Appl. No.: 229,889

[22] Filed: Apr. 19, 1994

[30] Foreign Application Priority Data

Jul. 12, 1993 [JP] Japan ................................ 5-171464

[51] Int. Cl.$^6$ ........................... B01D 21/00; B01D 24/48; C07C 37/68
[52] U.S. Cl. ............................... 210/299; 210/DIG. 5; 210/315; 210/484; 210/489; 422/270; 422/276; 568/754; 568/798
[58] Field of Search ................... 568/749, 754, 568/798; 422/101, 261, 267, 270, 276, 277; 210/198.1, 500.1, 500.23, DIG. 5, 299, 315, 484, 489

[56] References Cited

U.S. PATENT DOCUMENTS

| | | | |
|---|---|---|---|
| 4,080,296 | 3/1978 | Clark | 210/323 R |
| 4,102,785 | 7/1978 | Head | 210/65 |
| 4,361,481 | 11/1982 | Schnell | 210/85 |
| 4,609,465 | 9/1986 | Miller | 210/323.2 |
| 4,696,742 | 9/1987 | Smizaki | 210/287 |
| 4,919,860 | 4/1990 | Schindler et al. | 264/29.1 |
| 5,002,666 | 3/1991 | Matsumoto et al. | 210/321.61 |
| 5,089,135 | 2/1992 | Yonegama et al. | 210/500.23 |
| 5,092,990 | 3/1992 | Muramatsu et al. | 210/136 |
| 5,102,542 | 4/1992 | Lawrence et al. | 210/674 |
| 5,198,110 | 3/1993 | Harai et al. | 210/321.79 |

*Primary Examiner*—Robert J. Warden
*Assistant Examiner*—N. Bhat
*Attorney, Agent, or Firm*—Lowe, Price, LeBlanc & Becker

[57] ABSTRACT

An assembly for removing hydrophilic contaminants and a method of removing hydrophilic contaminants such as sodium included in an oil-state liquid using the removing assembly, which is able to remove positively the hydrophilic contaminants such as the sodium included in the oil-state liquid in each process of the plant such as a phenol producing apparatus as well as maintain a certain level of the removing performance for a long duration, consisting of: a coalescing element for coalescing and separating from the oil-state liquid the moisture including the hydrophilic contaminants such as sodium by being penetrated the fiber layer having the characteristics of alkali resistance and solvent resistance, typified by a carbon fiber; a liquid feeding means for feeding and supplying a mixed liquid of the moisture including the hydrophilic contaminants and the oil-state liquid; a water collecting means for collecting the moisture including the hydrophilic contaminants which is coalesced and separated; and a oil collecting means for collecting the oil-state liquid from which the moisture including the hydrophilic contaminants is separated and removed.

6 Claims, 8 Drawing Sheets

ASSEMBLY FOR REMOVING HYDROPHILIC CONTAMINANTS, METHOD OF THE SAME, AND APPARATUS FOR PRODUCING PHENOL

BACKGROUND OF THE INVENTION

1. Field of the Invention

This invention relates to a assembly for removing hydrophilic contaminants such as sodium, a method of the same, and an apparatus for producing phenol, which is utilized for removing the hydrophilic contaminants such as the sodium included in an oil-state liquid in each process of the plant as the phenol producing apparatus.

2. Description of the Related Art

In a phenol plant for producing the phenol, recently, a cumene method of which reaction condition is moderate and of which process can be completely automated is suitable for the continuous mass production as well as has excellent profitability, so that the method becomes a major phenol producing method in the world.

In the process of producing phenol by the cumene method, alkali such as sodium carbonate is added in the neutralization process after the oxidation of the cumene or in the neutralization process after cumene hydroperoxide which is obtained by oxidation of the cumene being disintegrated by an acid material.

However, the alkali used for the neutralization as described above may result in various problems downstream of the neutralization process. That is, when the oil-state liquid flowing in the process is heated by a reboiler which is equipped in a concentration tower or a distillation tower provided downstream of each neutralization process, the disadvantage that the sodium used for the neutralization is extracted and the fouling (clogging-up) in tube of reboiler tales place.

The fouling of the reboiler as described above causes a lowering in heat efficiency of the reboiler or an increase of chest pressure, so that the cleaning shut down of the reboiler have to be done, stopped each apparatus of the plant in every fixed period such as once in two or three months to maintain the function of the reboiler. Resultingly, it causes the lowering of productivity as well as the disadvantage that the work of the cleaning shut down itself is undesirable because of the hazardousness of the oil-state liquid to be dealt with such as the cumene.

There has heretofore been adopted the removing alkali such as sodium from the process by each kind of fluid treatment device.

As one of the fluid treatment devices, a filter device of so-called filling filter member system in which the filter member such as glass wool is filled in a drum and so on.

There is also a known filter device in which a cartridge type fluid filtration element called a depth-type element is attached. The cartridge type fluid filtration element is generally constructed in such a way that a filter member such as glass wool is wounded with almost uniform thickness as layers around the exterior of a porous holding cylinder, and doughnut disk-like end plates are fixed to both end surfaces of the filter member. There has been adopted a means for fixedly sealing the end plates to the filter member with a synthetic resin bonding agent such as a epoxy resin.

However, the method for removing alkali such as sodium by the filter device of filling filter member system as described above involves a disadvantage that the filter member such as glass wool tends to be melted as it has non-alkali resistance, whereby it can not maintain the performance as the filter member for a long duration.

In the filling filter member system, the filter member is directly filled in the drum and so on, so that the density of the filter member becomes irregular and the sufficient performance can not be obtained. Furthermore, the oil-state liquid is leaked from the gap formed at the contacted portion of the filled filter member and the drum body, so that the alkali such as the sodium can not be removed sufficiently.

In the method of removing alkali by the filter device in which the cartridge type fluid filtration element is attached, the irregularity of the density of the filter member can be improved because the filter member is wound on the exterior of the porous holding cylinder, however there is a disadvantage that the synthetic resin bonding agent such as the epoxy resin used for fixing the end plates to the filter member is melted due to acetone, cumene, cumene hydroperoxide, and phenol which are dealt with in the plant, so that the end plates can not be sealed completely to the filter member.

The object of the present invention is to provide an assembly for removing hydrophilic contaminants and the method of the same which can remove the hydrophilic contaminants such as sodium included in the oil-state liquid positively, as well as maintain the fixed removing performance for a long duration, and to provide a phenol producing apparatus which has high rate of operation.

SUMMARY OF THE INVENTION

The present invention is provided to attain the above object by positively separating and removing a hydrophilic contaminants such as sodium included in a oil-state liquid with water through a fiber layer which forms capillary tubes therein.

Concretely, this invention relates to a hydrophilic contaminants removing assembly which separates and removes a moisture including the hydrophilic contaminants from the oil-state liquid consisting of a coalescing means for coalescing and separating the moisture including hydrophilic contaminants from the oil-state liquid, a liquid feeding means for feeding and supplying the mixed liquid of the moisture including hydrophilic contaminants and the oil-state liquid to the coalescing means, a water collecting means for collecting the moisture including hydrophilic contaminants which is collected and removed; and a oil collecting means for collecting oil-state liquid from which the moisture including hydrophilic contaminants is separated and removed, and wherein the coalescing means includes a fiber layer forming capillary tubes and has characteristics of alkali resistance and solvent resistance.

The fiber diameter of the fiber layer is preferably 1–100 μm, and more preferably 4–20 μm.

The hydrophilic contaminants removing assembly of the present invention is characterized by the fiber layer including a carbon fiber.

The hydrophilic contaminants removing assembly according to the present invention is characterized by the coalescing means including a cylindrical-shaped porous holding cylinder for holding the fiber layer, which can be connected and disconnected from the main body of the assembly with the fiber layer wound around the outer peripheries thereof.

The hydrophilic contaminants removing assembly according to the present invention is characterized by the coalescing means including end plates which are attached to the both end surfaces of the fiber layer and provided with a endless ring-shaped thin protrusion protruding to the side of the fiber layer, and wherein the fiber layer has a highly densified portion having high fiber density at the both ends thereof into which the protrusion is cut into.

The present invention is a phenol producing apparatus including a reaction tower for forming cumene by benzene and propylene, an oxidation tower for forming cumene hydroperoxide by oxidizing the cumene at downstream of the reaction tower, a concentration tower for concentrating the cumene hydroperoxide at downstream of the oxidation tower, a disintegration tower for forming coarse phenol and coarse acetone by disintegrating the concentrated cumene hydroperoxide by the acid material at down stream of the concentration tower and each kinds of distillation tower for separating and refining the coarse phenol and the coarse acetone at downstream of the disintegration tower, which is provided with the hydrophilic contaminants removing assembly in at least one portion on the passage between the oxidation tower and the concentration tower, between the disintegration tower and the distillation tower, or on the passage provided for feeding back the excess cumene from the concentration tower to the upstream side of the oxidation tower.

This invention is a hydrophilic contaminants removing method for separating and removing the hydrophilic contaminants included in the oil-state liquid which is dealt with in the plant such as phenol producing apparatus including the steps of; the water is added to the oil-state liquid, the hydrophilic contaminants in the oil-state liquid is shifted and extracted into the water, and the moisture including the hydrophilic contaminants is penetrated in the fiber layer forming capillary tubes to be coalesced and separated.

The hydrophilic contaminants removing method of the present invention further includes the steps of: a part of the moisture including the hydrophilic contaminants which is coalesced and separated by being penetrated in the fiber layer is blowed; and the rest is utilized as the water for being added into the oil-state liquid.

In the hydrophilic contaminants removing method of the present invention, the oil-state liquid is a mixed liquid including a coarse phenol and a coarse acetone obtained by disintegrating the cumene hydroperoxide.

In the above method, the water corresponding to 5–20% of the oil-state liquid volume is added to the oil-state liquid including the coarse phenol and the coarse acetone, and preferably the mixed liquid of the water and the oil-state liquid is stirred with the adding of the water or after the adding of the water.

The hydrophilic contaminants removing assembly of the present invention is characterized by the oil-state liquid is the mixed liquid including cumene and cumene hydroperoxide obtained by oxidizing the cumene.

According to the present invention thus described, the water including hydrophilic contaminants is separated from the oil-state liquid by the steps of: the hydrophilic contaminants such as sodium included in the oil-state liquid is shifted and extracted into the water; the mixed liquid of the water including the hydrophilic contaminants and the oil-state liquid is fed to the coalescing means by the liquid feeding means; and penetrated in the capillary tubes formed in the fiber layer of the coalescing means to make the water including the hydrophilic contaminants coalesce and grow in the fiber layer.

In the above phase, the fiber layer is constructed by the fiber having the characteristics of alkali resistance and solvent resistance such as carbon fiber, so that the fiber is not dissolved even in the case that the hydrophilic contaminants included in the oil-state liquid is alkali such as sodium, and the performance of the coalescing means for coalescing and separating can be maintained stably for a long duration.

Next, the oil-state liquid is collected by the oil collecting means whereas the water including the hydrophilic contaminants is collected and removed by the water collecting means.

The fiber layer is wound around the outer peripheries of the cylindrical-shaped porous holding cylinder which is connected and disconnected and the coalescing means employs so-called depth-type cartridge system, whereby the fiber layer can be formed by winding on the holding cylinder as well as the winding work for forming the fiber layer can be performed at outside of the assembly, resultingly the fiber layer is formed with almost uniform density and thickness. Therefore it solves the ununiformity of the filter member density as the conventional filter employing the filling filter member described above as well as solve the disadvantage that the oil-state liquid leaks from the gap between the connected portion of the filter member and the drum body as the conventional filter employing the filling filter member, as a result, the sufficient separating and removing performance is able to be obtained.

The fiber layer and the end plates are attached firmly by the protrusion of the end plates cutting into the highly densified portion formed at both end surfaces of the fiber layer, whereby solves the disadvantage of the dissolution of the bonding agent for attaching the end plates and the filter member as the conventional cartridge-type fluid filtration element.

If the water is added positively in the oil-state liquid at the upstream side of the hydrophilic contaminants assembly according to the concentration of the dydrophiclie contaminants to be removed from the oil-state liquid, the hydrophilic contaminants are shifted and extracted to the water positively, as a result, they will be removed from the oil-state liquid certainly.

When the oil-state liquid is the mixed liquid including the coarse phenol and the coarse acetone obtained by disintegrating the cumene hydroperoxide, the water corresponding to 5–10% of the oil-state liquid volume is added and the mixed liquid of the water and the oil-state liquid is stirred with the adding of the water or the after the adding of the water, so that the hydrophilic contaminants can be shifted and extracted into the water more positively.

Furthermore, part of the removed water including the hydrophilic contaminants is blowed and the rest is utilized as the water for being added to the oil-state liquid at the upstream side of the hydrophilic contaminants assembly, whereby a large quantity of water is not necessary in the treatment of adding water and the cost can be reduced.

The hydrophilic contaminants removing assembly is installed at each place of the phenol producing apparatus, for example, on the passage between the oxidation tower and the concentration tower, on the passage between the disintegration tower and the distillation tower, or on the passage provided for feeding back the excess cumene from the concentration tower to the upstream side of the oxidation tower, so that the stoppage time by the cleaning shut down can be reduced and the operation rate of the phenol producing apparatus can be improved, resultingly the above-mentioned object can be achieved.

Figure 1:
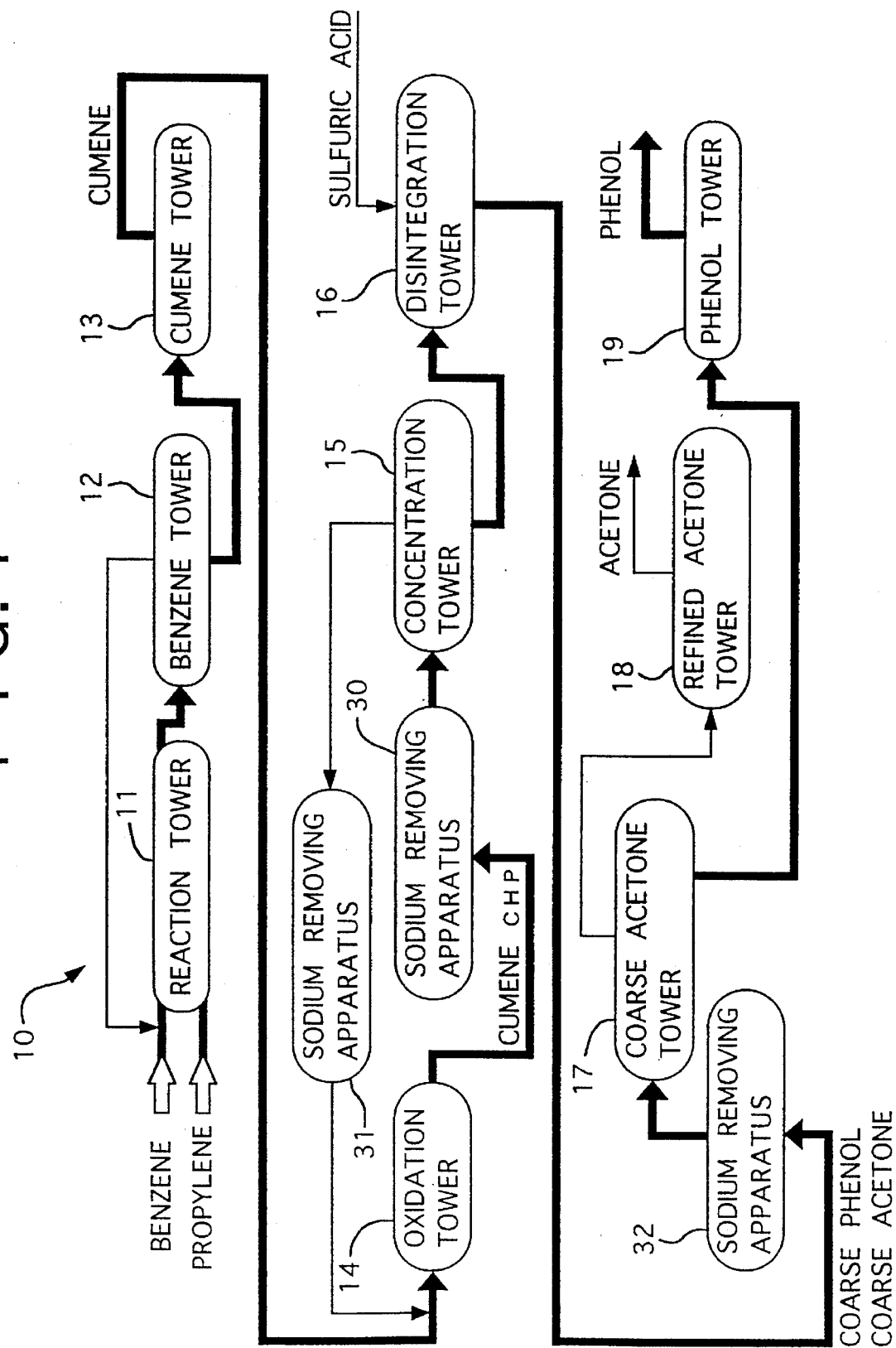
FIG. 1 is a view of entire structure of a phenol producing apparatus as one embodiment of the present invention.

Certain terminology will be used in the following description for convenience in reference only and will not be limiting. The words "up", "down", "right", and "left" will designated directions in the drawings to which reference is made. The words "in" and "out" will refer to direction towards and away from, respectively, the geometric center of the device and designated parts thereof. Such terminology will include derivatives and words of similar import.

DETAILED DESCRIPTION OF THE PREFERRED EMBODIMENT

The preferred embodiment of the present invention will now be described with reference to the drawings.

FIG. 1 depicts a whole diagrammatic structure of a phenol producing apparatus 10 in the most preferable embodiment according to the present invention.

The phenol producing apparatus 10, from an upstream side (the left side in the drawing), has a reaction tower 11 in which benzene reacts with propylene as raw materials to form so-called cumene isopropylbenzene, an oxidation tower 14 which oxidizes therein the cumene via a benzene tower 12 and a cumene tower 13 to form cumene hydroperoxide (CHP), a sodium removing apparatus 30 which separates and removes sodium mixed into for neutralization, a concentration tower 15 which concentrates cumene hydroperoxide, a sodium removing apparatus 31 provided on the way back from the concentration tower 15 to the upstream side of the oxidation tower 14, a disintegration tower 16 which disintegrates the concentrated cumene hydroperoxide by an acid material to form coarse phenol and coarse acetone, a sodium removing apparatus 32, and a coarse acetone tower 17, a refined acetone tower 18, a phenol tower 19 which are each kinds of distilled tower for separating and refining phenol and acetone.

The cumene formed in the reaction tower 11 is fed into the benzene tower 12 with unreacted benzene. The unreacted benzene is fed back to the upstream side of the reaction tower 11 whereas the cumene is fed downstream to the cumene tower 13 and retained therein to be fed to the oxidation tower 14.

Figure 2:
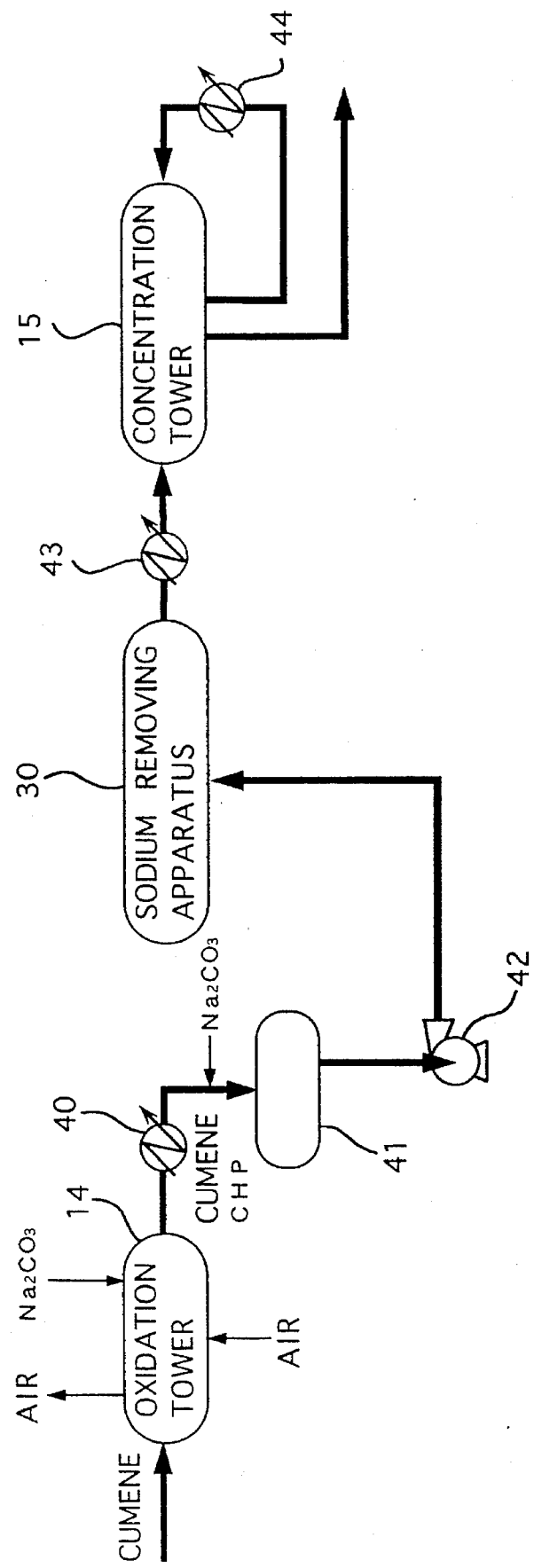
FIG. 2 is a detailed block diagram of the first fragmentary portion of the above embodiment.

FIG. 2 depicts an oxidation process and a neutralization process from the oxidation tower 14 down to the concentration tower 15 in detail.

A settler 41 via a heat exchanging device 40 is provided at downstream of the oxidation tower 14, and a sodium removing apparatus 30 via a pump 42 is provided at downstream of the settler 41. The sodium removing apparatus 30 is further related to the concentration tower 15 provided at downstream thereof via a heat exchanging instrument 43.

The concentration tower 15 is provided with a reboiler 44 for heating.

Into the oxidation tower 14, air as a oxidizer and sodium carbonate ($Na_2CO_3$) are added to form cumene hydroperoxide resulting from the typical radical chain reaction. The cumene is usually oxidized into the cumene hydroperoxide by 20–22% of oxidation density.

Then, sodium carbonate ($Na_2CO_3$) for neutralization is added to the oil-state liquid defined by the CHP made by oxidation and the cumene, and the liquid is retained in the settler 41. Incidentally, the treatment of adding water can be optionally performed suitably according to the concentration of sodium along with the adding of sodium carbonate, though the treatment is not always necessary as the oil-state liquid includes much moisture. For the water to be added in this treatment, the one including sodium which is separated and removed by the sodium removing apparatus 30 can be utilized once again.

The sodium included in the oil-state liquid after the neutralization by sodium carbonate is moved and extracted into the water in the oil-state liquid. The oil-state liquid containing the CHP and the cumene in the condition emulsified by the water including sodium is fed to the sodium removing apparatus 30 by the pump 42 to become the condition including only the oil-state liquid, the water including sodium being separated therefrom by passing through the sodium removing apparatus 30, and fed downstream into the concentration tower 15.

As one example of the operating condition for the plant in these oxidation and neutralization processes, the fluid is of the oil-state liquid containing the cumene and the CHP (about 20–22% of oxidation density), and the specific gravity thereof is about 0.9, the viscosity is about 2 cp, the rate of flow is about 130 ton/h, the operating pressure is about 2 $kg/cm^2$ and the operating temperature is about 40° C.

As for the content of sodium in the oil-state liquid before and after the sodium removing apparatus 30, for example, 10 ppm becomes less than 1 ppm.

Figure 3:
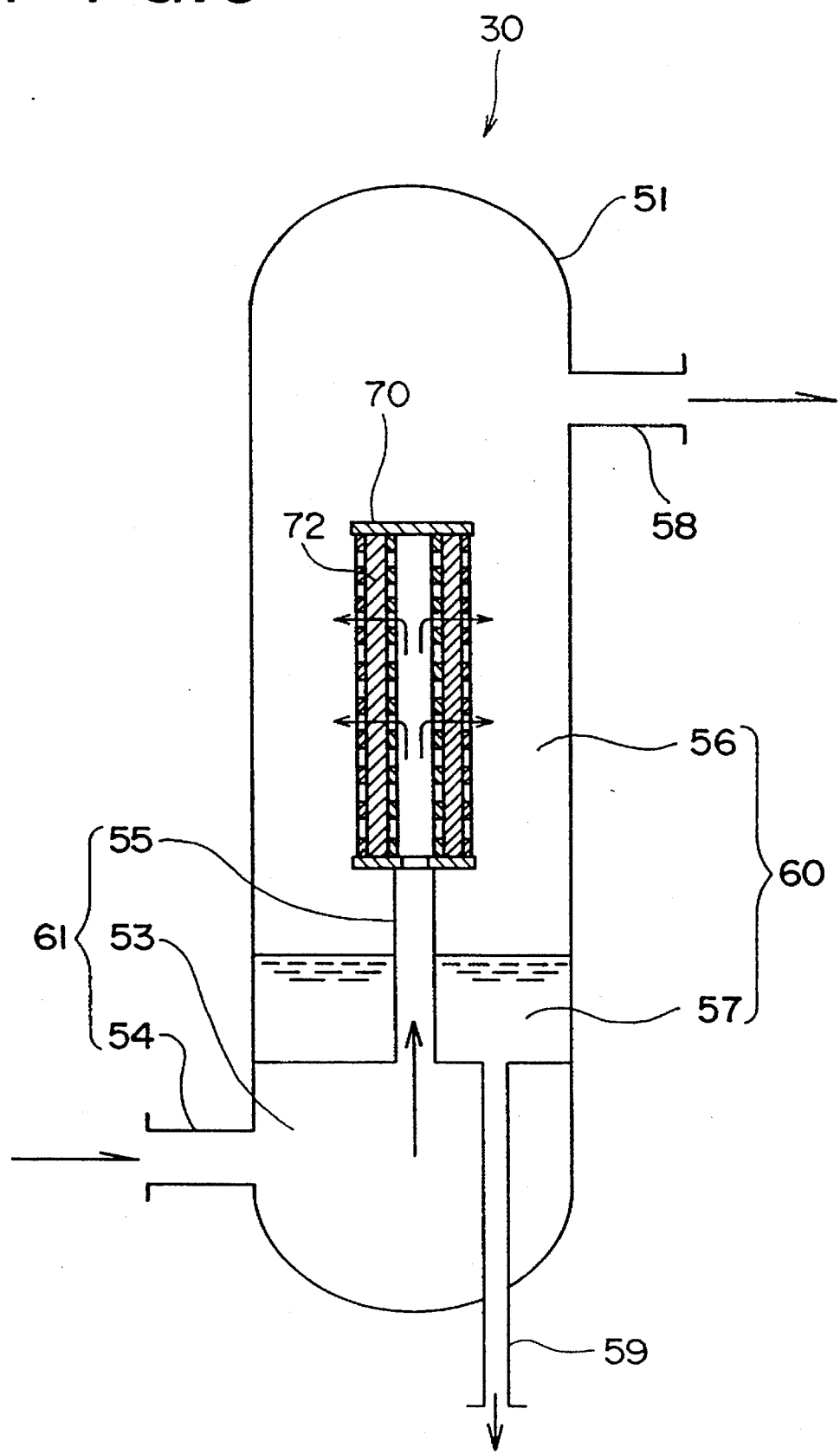
FIG. 3 is a schematic representation diagram of a sodium removing apparatus installed and used for the above embodiment.

FIG. 3 depicts the detailed structure of the sodium removing apparatus 30 as the hydrophilic contaminants removing assembly.

The sodium removing apparatus 30 is covered by a casing 51 at the outside. At the central portion of the casing therein, a coalescing element 70 is provided, as a coalescing means for coalescing moisture including sodium to separate from the oil-state liquid. In FIG. 3, one coalescing element 70 is provided at the central portion, but plural numbers of the same elements can be assembled, for example, scores of coalescing elements are provided in the large-sized casing 51 of which external diameter is about 3 mm.

In the bottom of the casing 51, a mixed liquid chamber 53 for collecting the mixed liquid of the moisture including sodium and the oil-state liquid and supplying them to the coalescing element 70 is provided, an inlet nozzle 54 for introducing therein the mixed liquid from the upstream side is provided at the side surface of the mixed liquid chamber 53, and a connecting passage 55 connecting with the coalescing element 70 is extended from the upper surface of the mixed liquid chamber 53. The inlet nozzle 54, the mixed liquid chamber 53 and the connecting passage 55 will be referred to as a liquid feeding means 61, hereinafter.

A domain including the upper side of the mixed liquid chamber 53 inside the casing 51 as well as a periphery of the coalescing element 70 becomes a separated liquid chamber 60 for collecting the moisture including sodium and oil-state liquid which are separated through the coalescing element 70. During the operation of the plant, the separated liquid chamber 60 has two layers above and below, and the upper side layer becomes a oil-state liquid layer 56 after the moisture including sodium was separated and removed, whereas the lower side layer is a sedimentation layer 57 in which the water including sodium is sedimented.

At the upward portion of the casing 51, an outlet nozzle (oil collecting means) 58 feeding the oil-state liquid of the oil-state liquid layer 56 to the downstream side is provided, and a drainage (water collecting means) 59 draining the moisture including sodium of the sedimentation layer 57 to outside of the casing 51 is provided downward, piercing through the mixed liquid chamber 53.

The casing 51 is provided with an interface detecting means such as a level gage for detecting the position of the interface between the sedimentation layer 57 and the oil state liquid layer 56 not shown in drawings to thereby drain the water including sodium which is collected in the separated liquid chamber 60 inside the casing 51 from the drainage 59 suitably by means of a manual or controlled bulb.

Figure 4:
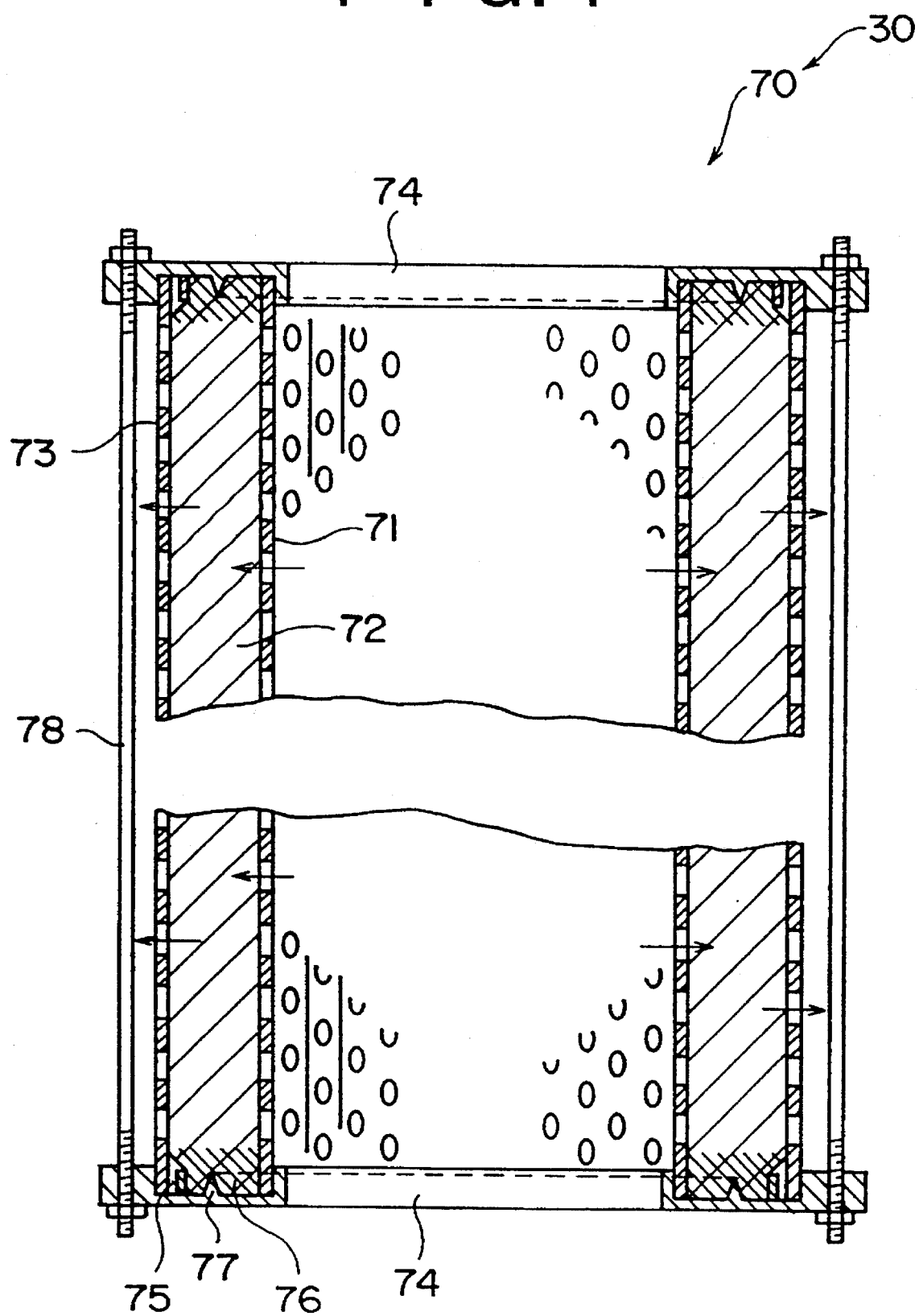
FIG. 4 is a vertical sectional view of the fragmentary portion of the sodium removing apparatus.
Figure 5:
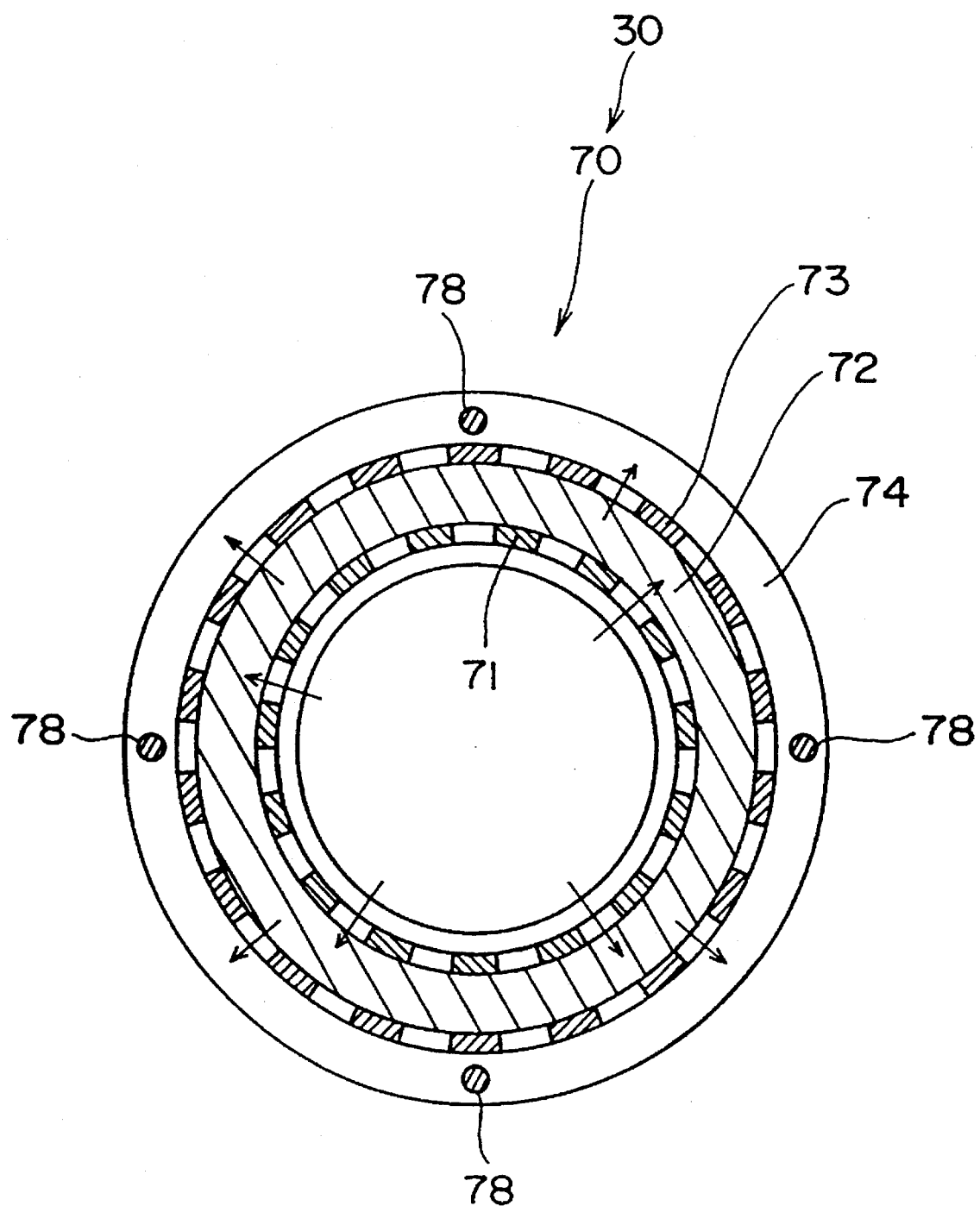
FIG. 5 is a horizontally sectional view of the fragmentary portion of the sodium removing apparatus.

FIG. 4 and FIG. 5 depict the detailed structure of the coalescing element 70. FIG. 4 is a longitudinal sectional view and FIG. 5 is a horizontal sectional view.

The coalescing element 70 has at the central portion therein a cylindrically shaped porous holding cylinder 71 made of a metallic punch plate or synthetic resin and so on.

Around the outer peripheries of the holding cylinder 71, a filter member 72 as a fiber layer having almost uniform density and thickness is provided. The material of the filter member 72 is a carbon fiber characterized by alkali resistance, acid resistance and solvent resistance. In the filter member 72, the gap between each fibers resembles capillary tubes. The layer thickness of the filter member 72 is generally 10–50 mm, but it should not be considered to be limited by this range. The diameters of the fiber the thickness of the fiber is preferably about 1–100 μm, and more preferably 4–20 μm.

At the outer peripheries of the filer media 72, a cylindrical shaped porous outer cylinder 73 made of a metallic punch plate and so on is provided.

End plates 74 having disc-like configuration are attached on both ends of top and bottom of the holding cylinder 71, the filter member 72 and the outer cylinder 73 as can be seen in FIG. 4.

Furthermore, a narrow metallic bands 75 are wound around the outer peripheries of both top and bottom end portions of the filter member 72. The both top and bottom end portions of the filter member 72 is compressed by tightening the band 75 to form highly densified portions 76 to hinder the permeation of the fluid.

The end plates 74 has a endless ring-shaped thin protrusion 77 which protrudes into the filter member 72. The end plates 74 attached at both top and bottom ends of the coalescing element 70 are tightened each other by suitable numbers of bolt 78 in a state the protrusion 77 is cut into the highly densified portion 76, whereby both top and bottom ends of the filter member 72 are integrated with to the end plates 74.

The coalescing element 70 employs a cartridge system which can be connected and disconnected easily from the main body of the sodium removing apparatus 30 to thereby prevent the clogging-up state of the filter member 72 because of a long time use thereof by changing with the new one. Only the filter member 72 could be changed.

In the sodium removing apparatus 30 as has been described above, the moisture including sodium will be removed from the oil-state liquid as follows.

First, the mixed liquid consisting of the moisture including sodium and the oil-state liquid is introduced from the inlet nozzle 54 to the mixed liquid chamber 53, and fed out to the coalescing element 70 through the connecting passage 55.

Figure 6:
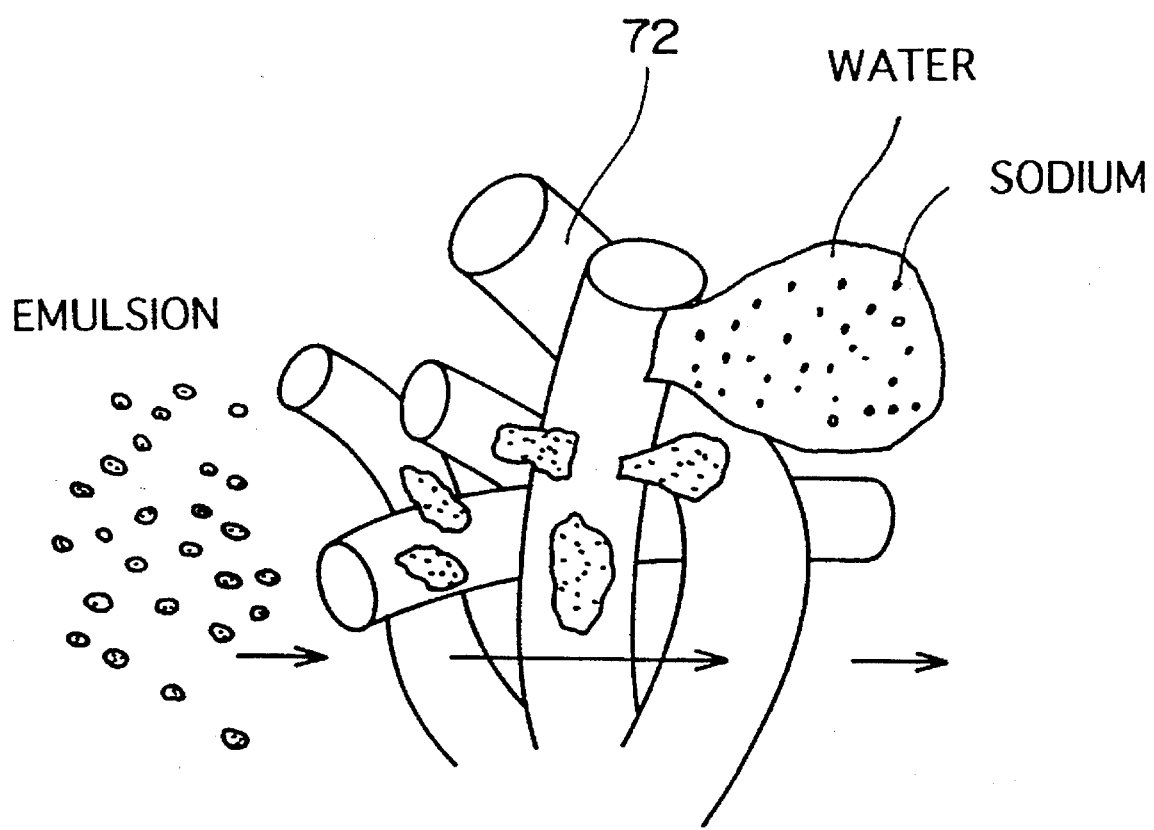
FIG. 6 is a view for depicting the coalescent and separation by the sodium removing apparatus.

Next, the mixed liquid is separated into the moisture including sodium and the oil-state liquid in the coalescing element 70. In the coalescing instrument 70, the mixed liquid is infiltrated into the filter member 72 from inside of the holding cylinder 71 through the pores thereof, and penetrated in the filter member 72 from the inside to the outside thereof to be fed to the outer separated liquid chamber 60 through the pores of the outer cylinder 73. As can be seen in FIG. 6, the moisture including sodium mixed in the oil-state liquid is coalesced while the mixed liquid is penetrated in the filter member 72.

In FIG. 6, the emulsion (the left side on the drawing) in a state the moisture including sodium is dispersing to the size of about 1 μm–10 μm is broken by utilizing the fiber activity of the filter member 72. After that, the moisture including sodium is coalesced in the capillary tubes formed at the gap of the fiber of the filter member 72. The moisture including sodium grows according as moving to the left side on the drawing without being broken by the flow because of the surface tension between the oil-state liquid and water, to be the water droplets including sodium of which diameters is about 2 mm–6 mm until it penetrates to the outer surface of the filter member 72.

The water droplets including sodium which have grown from the diameters of micron unit to the diameters of mill unit are passed through the pores of the outer cylinder 73 and separated from the oil-state liquid, being sedimented by the difference of specific gravity to thereby form the sedimentation layer 57 at the bottom portion of the separated liquid chamber 60 at the peripheral of the coalescing element 70 whereas the oil-state liquid layer 56 from which the moisture including sodium is separated and removed is formed at the upper side of the sedimentation layer 57.

Then, the water including sodium in the sedimentation layer 57 is drained from the draining passage 59 to the outside of the sodium removing apparatus 30, whereas the almost pure oil-state liquid in the oil-state liquid layer 56 is fed to the downstream side from the outlet nozzle 58.

As has been described above, the sodium included in the oil-state liquid is removed with water by means of the sodium removing apparatus 30, as a result, the concentration of sodium in the oil-state liquid is decreased less than 1/10.

Figure 7:
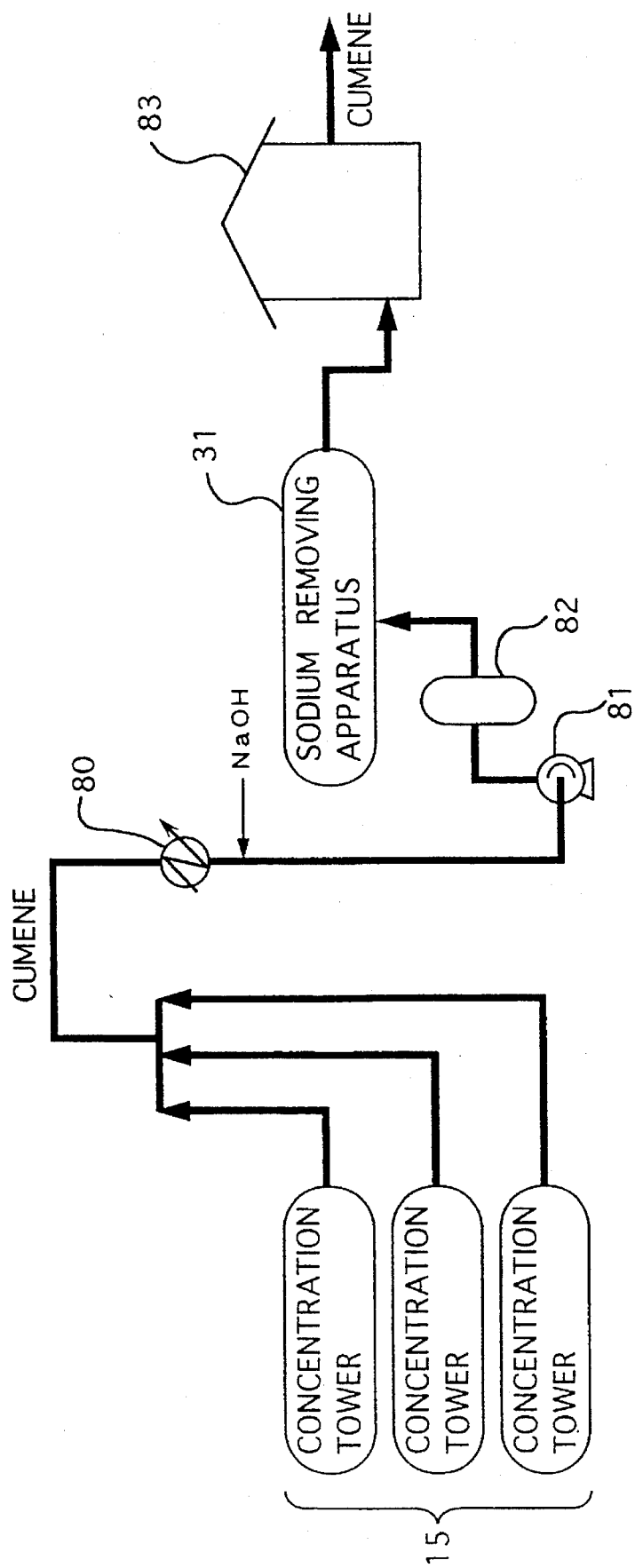
FIG. 7 is a detailed block diagram of the second fragmentary portion of the above embodiment.

FIG. 7 depicts the passage (the recycle process) through which the excess cumene is fed back from the concentration tower 15 to the upstream side of the oxidation tower 14 (see FIG. 1) in detail.

The sodium removing apparatus 31 is provided at the downstream of the concentration tower 15 shown on the left side in the drawing via a heat exchanging device 80, pump 81, and a pre-filter 82 in sequence. The structure and operation of the sodium removing apparatus 31 is same as these of the sodium removing apparatus 30 described above. A tank 83 is provided at downstream of the sodium removing apparatus 31, and the downstream side of the tank 83 is related to the upstream side of the oxidation tower 14 shown in FIG. 1.

In the concentration tower 15, the oil-state liquid containing the CHP and the cumene is concentrated to increase the concentration degree of the CHP. At this phase, the cumene tends to distilled at the top portion in the concentration tower 15. As this excess cumene includes some phenol, water solution of caustic soda (NaOH) of 20–22% concentration is added to remove phenol.

Next, the cumene into which the water solution of caustic soda has already been added is fed to the pre-filter 82 by the pump 81 to be filtrated and removed dust therefrom, and further fed to the sodium removing apparatus 31. In the sodium removing apparatus 31, the sodium is removed from the cumene by separating the sodium included in the cumene with water.

The cumene from which sodium is separated and removed in the sodium removing apparatus 31 is retained in the tank 83 to be almost complete condition, thereafter fed to the upstream side of the oxidation tower 14 as shown in FIG. 1 to be utilized again.

In FIG. 1, returning to the description of the main way, the oil-state liquid defined by the CHP and the cumene after the sodium is removed therefrom by means of the sodium removing apparatus 30 is concentrated in the concentration tower 15 and fed to the disintegration tower 16.

Figure 8:
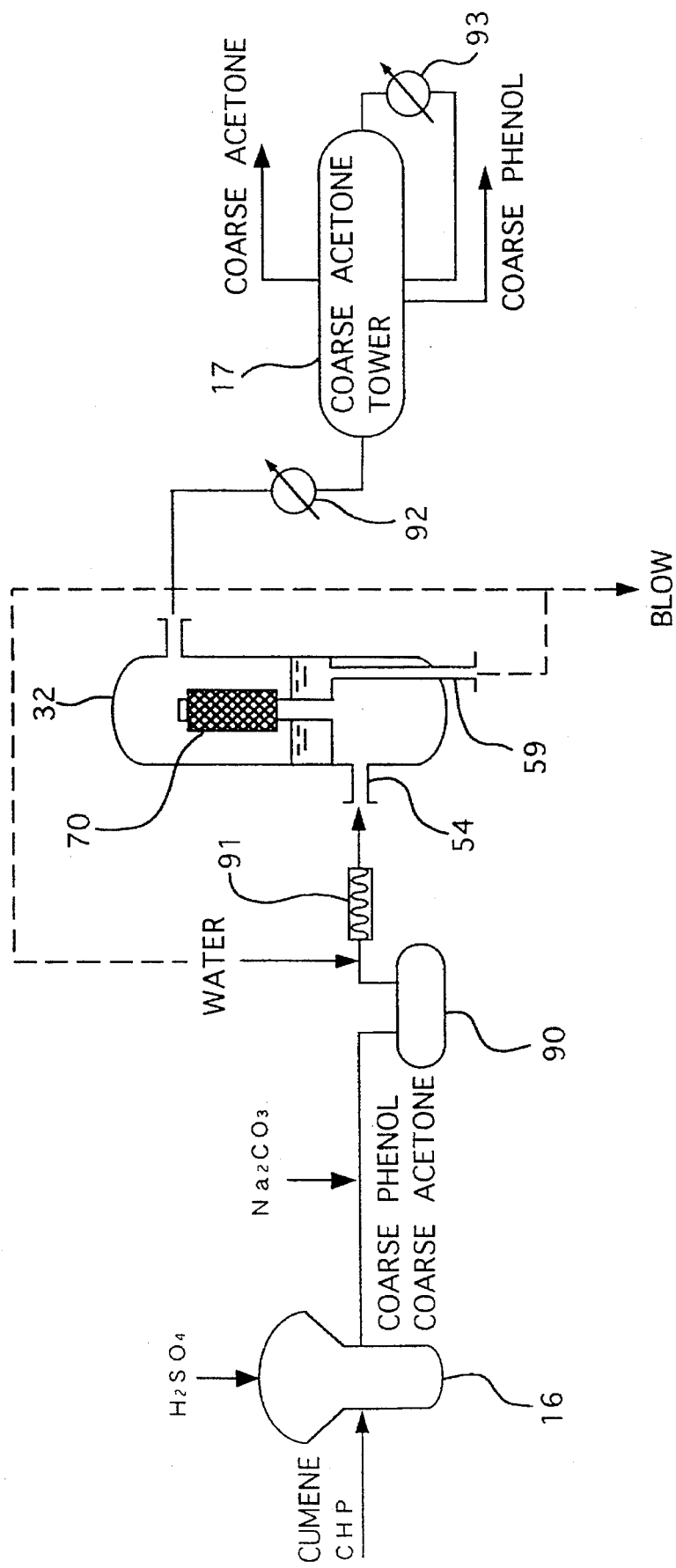
FIG. 8 is a detailed block diagram of the third fragmentary portion of the above embodiment.

FIG. 8 depicts the detailed structure from the disintegration tower 16 to the coarse acetone tower 17 which forms the distillation system.

A settler 90 is provided at downstream of the disintegration tower (cleavage) 16 shown on the left side in the drawing, and the sodium removing apparatus 32 is further provided at downstream of the settler 90 via a static mixer 91. The structure and operation of the sodium removing apparatus 32 is same as these of the sodium removing apparatus 30 described above. The sodium removing apparatus 32 is connected to the coarse acetone tower 17 via a heat exchanging device 92. The coarse acetone tower 17 is provided with a reboiler 93 for heating.

In the disintegration tower 16, the CHP is disintegrated by sulfuric acid ($H_2SO_4$) as catalyst. Almost 100% of the CHP is disintegrated in this phase, resultingly the coarse acetone and the coarse phenol are formed. The material formed by disintegration by the acid material including these coarse acetone and the coarse phenol is added thereinto the sodium carbonate ($Na_2CO_3$) and retained in the settler 90.

At the downstream of the settler 90, water is added in the oil-state liquid after the adding of the sodium carbonate thereinto (of which main components are the coarse acetone and the coarse phenol), and the mixed liquid of the oil-state liquid and the water is stirred by the static mixer 91 to be fed to the sodium removing apparatus 32. The sodium in the oil-state liquid is shifted and extracted into the added water so that the oil-state liquid is in the condition emulsified by the water including the sodium.

The preferable volume of the water to be added should correspond to 5–20% of the oil-state liquid volume. The stirring means of the mixed liquid after the adding of water is not limited to be the static mixer 91 and can be replaced with other devices such as a pump.

In the sodium removing apparatus 32, as same as the above-mentioned oxidation process shown on FIG. 2, the water including sodium after the emulsion has been broken is coalesced and separated from the oil-state liquid by the coalescing device 70 provided in the sodium removing apparatus 32, whereby the sodium is removed from the oil-state liquid.

The oil-state liquid from which the water including sodium is separated and removed by the sodium removing apparatus 32 is fed to the coarse acetone tower 17, where it is separated into the coarse acetone and the coarse phenol.

On the other hand, part of the water including sodium which is drained from the drainage 59 is blowed, and the rest thereof is desirable to be utilized again as the water for the sodium being moved and extracted thereinto, added to the upstream of the sodium removing apparatus 32 (an alternate long and short dash line in the drawing). The pure water corresponding to the thus-blowed volume are added with the water including sodium utilized again to the upstream side of the sodium removing apparatus 32. The blowed volume is, for example, 10% of the whole volume of the water including sodium which is drained from the drainage 59. According to this treatment, a large quantity of water is not necessary, and the volume of acetone outflowing into the water can be reduced to the minimum, resultingly the concentration of the sodium which is introduced from the inlet nozzle 54 of the sodium removing apparatus 32 can be maintained in a certain level.

As can be seen in FIG. 1, the coarse acetone which is distilled at the top portion in the coarse acetone tower 17 is fed to the refined acetone tower 18 and refined therein to be the acetone as a product, whereas the coarse phenol which is separated from the coarse acetone in the coarse acetone tower 17 is refined in the phenol tower 19 to be the phenol as a product.

According to the present embodiment, following effects can be attained.

The material of the filter member 72 used for the coalescing element 70 is the carbon fiber having the characteristics of alkali resistance, the acid resistance and the solvent resistance, so that the fiber is not dissolved due to the sodium included in the oil-state liquid and the performance of the coalescing element 70 for coalescing and separating can be maintained for a long period of time.

Each sodium removing apparatus 30, 31, 32 has therein the coalescing element 70 employing so-called depth-type cartridge system of which the filter member 72 has almost uniform density and thickness as compared with the conventional filter employing a filling filter member system as described above, so that it displays the high-efficient function of coalescing and separating, and it can further solve the disadvantage that the oil-state liquid leaks from the gap between the connected portion of the filter member and the drum body as the conventional filter employing the filling filter member system.

The end plates 74 of the coalescing element 70 are attached firmly to the both top and bottom end surfaces of the filter member 72 by the protrusion 77 cutting into the highly densified portion 76, so that it solves the disadvantage that the bonding agent of synthetic resin such as epoxy resin is dissolved by the acetone, the cumene, the cumene hydroperoxide and the phenol as the conventional cartridge-type filter described above.

Incidentally, each sodium removing apparatus 30, 31, 32 is simple in structure, having no rotating portion, so that it can be installed in the already-established lines easily as well as be handled easily as the adjustment of operation after the installation is not necessary.

In the neutralization process after the disintegration of the CHP by the acid material as shown in FIG. 8, the oil-state liquid after the adding of the sodium carbonate thereinto (of which main components are the coarse acetone and the coarse phenol) is added the water thereinto in the upstream side of the sodium removing apparatus 32 and the mixed liquid of the oil-state liquid and the water is stirred in the static mixer 91, so that the sodium is shifted and extracted into the water positively and the performance of the sodium removing apparatus 32 can be improved.

The volume of the water to be added in the above-mentioned phase is made to be corresponded to 5–20% of the oil-state liquid volume, so that the effect is made to be more certain.

Furthermore, part of the water including sodium which is separated and removed by the sodium removing apparatus 32 is blowed, and the rest of it is utilized once again as the water to be added into the oil-state liquid in the upstream side of the sodium removing apparatus 32, whereby a large quantity of water is not necessary in the treatment of adding the water and the reduced cost can be achieved.

As the phenol producing apparatus 10 is provided with the sodium removing apparatus 30 on the passage between the oxidation tower 14 and the concentration tower 15, the sodium removing apparatus 32 on the passage between the disintegration tower 16 and the coarse acetone tower 17, and the sodium removing apparatus 31 on the passage feeding back the excess cumene from the concentration tower 15 to the upstream side of the oxidation tower 14, the sodium can be removed positively in each place.

Therefore, the sodium deposit at each reboiler 44, 93 provided for the concentration tower 15 and the coarse acetone tower 17 can be decreased, resultingly the fouling (dogging-up state) of tubes of each reboiler 44, 93 can be prevented.

Incidentally, the corrosion of each device member included in the phenol producing apparatus 10 can be decreased by the positive removal of the sodium.

As discussed above, the fouling of each reboiler 44, 93 in the concentration tower 15 and the coarse acetone tower 17 can be prevented, resultingly the frequency of cleaning shut down can be decreased.

Thus, the operating rate of the phenol producing apparatus 10 can be improved, the stoppage time being shorten, as well as the expense of direct work required for the cleaning shut down can be saved and the loss of the liquid to be dealt with can be reduced.

For example, the cleaning shut down which has been performed 4 to 6 times in a year can be decreased to the one to be performed 1 or 2 times in a year. The cleaning shut down for one time often requires the working hours for about two days, thus the reduction of one cleaning shut down makes the cost cut down for more than one hundred million yen.

The times of dealing with the cumene which is unstable and explosive as well as exerts bad influence on human body will be reduced by the reduction of times of performing the cleaning shut down, so that the safety aspect in the plant can be improved.

It is to be understood that the present invention is not limited to the above-described embodiment, including other structures to attain the purpose of the present invention, and variations or modifications as follows will be included in the present invention.

In the above-mentioned embodiment, each sodium removing apparatus 30, 31, 32 is the vertical device, but it may be the horizontal device, that is, the device may be the structure having the coalescing element 70 as the coalescing means therein, as well as forming the separated liquid chamber 60 at outside of the coalescing element 70 for collecting the oil-state liquid and the water including sodium after the separation.

In the above-mentioned embodiment, the coalescing element 70 shown in FIG. 3 has long and thin cylindrical shape, but it may have flat cylindrical shape. The shape of the holding cylinder 71 is not limited to be the cylindrical shape as in the above-mentioned embodiment, but it may be the tubular shape of which sectional configuration will be oval or polygon, namely, it should be formed almost cylindrical shape.

Furthermore, in the above-mentioned embodiment, the respective sodium removing apparatus 30, 31, 32 are provided on the passage between the oxidation tower 14 and the concentration tower 10 of the phenol producing apparatus 10, on the passage between the disintegration tower 16 and the coarse acetone tower 17 and on the passage returning the excess cumene to the upstream side of the oxidation tower 14, but more than two apparatus should be provided on each place.

When the several numbers of the sodium removing apparatus are provided as described above, they may be provided sequentially or inserted between other devices such as settler.

In the above-mentioned embodiment, the material of the filter member 72 of the coalescing element 70 was explained as to be carbon fiber, but it is not limited to that and may be the carbon fiber synthesized with other fiber such as polypropylene, namely, the fiber having the characteristics of alkali resistance and solvent resistance.

The forming method for the fiber layer is optional, for example, the sheet-like filter member are wrapped in many sheets so as to reach the fiber layer of the designated thickness. Otherwise, the plural layers may be made by the filter member of different kinds of material.

The hydrophilic contaminants removing assembly in the above described embodiment is the sodium removing apparatus 30, 31, 32 which removes sodium of the sodium carbonate or the caustic soda which are added to the oil-state liquid in the neutralization process of the phenol plant, but the hydrophilic contaminants removed by the hydrophilic contaminants removing assembly in the present invention is not limited to the sodium but may be other alkaline metal such as potassium or alkaline earth metal such as calcium, that is, the contaminants having hydrophilic property which can be shifted and extracted into the water.

In addition, the hydrophilic contaminants removing assembly in the present invention is used not only for the phenol producing apparatus 10 as the above-mentioned embodiment but also for other similar plant such as cresol producing plant.

As discussed above in accordance with the present invention, the fiber layer forming the capillary tubes in the hydrophilic contaminants removing assembly has the characteristics of alkaline resistance and solvent resistance, so that the hydrophilic contaminants such as the sodium included in the oil-state liquid can be removed positively and the removing performance of the assembly can be maintained for a long period of time. As the density of fiber layer is made to be uniform because of the coalescing means employing the cartridge system, the performance of the assembly for removing hydrophilic contaminants can be improved further. In addition, the operation rate of the plant can be improved when the inventive hydrophilic removing assembly is installed in the plant such as the phenol producing plant.

What is claimed is:

1. A hydrophilic contaminants removing apparatus for removing moisture including the hydrophilic contaminants from a mixed liquid, the mixed liquid including the moisture and an oil-state liquid, the apparatus comprising:

a chamber containing the mixed liquid, means for supplying the mixed liquid from the chamber to a coalescing means, coalescing means for coalescing and separating the moisture from the mixed liquid resulting in the oil-state liquid, the oil-state liquid and the moisture being released from the coalescing means into a separated liquid chamber, the moisture forming a water sedimentation layer at a bottom portion of the separated liquid chamber, means cooperating with the bottom portion of the separated liquid chamber for collecting the water sedimentation layer; and means cooperating with an upper portion of the separated liquid chamber for collecting the oil-state liquid;

wherein the coalescing means comprises:

an alkali resistant and solvent resistant fiber layer including capillary tubes, a cylindrical shaped porous holding cylinder having end portions connectable and disconnectable from a main body of the removing apparatus, wherein the fiber layer is wound about the outer peripheries of the holding cylinder so as to be held by the cylinder, the fiber layer including a highly densified portion formed at the end portions, and end plates attached to both end portions and including an endless ring-shaped thin protrusion protruding toward and cutting into the highly densified portion of the fiber layer.

2. The hydrophilic contaminants removing assembly according to claim 1, wherein the fiber layer includes a carbon fiber.

3. The hydrophilic contaminants removing assembly according to claim 1, wherein the fiber layer has 1–100 μm diameters.

4. A phenol producing apparatus including a reaction tower for forming cumene by benzene and propylene, an oxidation tower for forming a cumene hydroperoxide by oxidizing the cumene at downstream of the reaction tower, a concentration tower for concentrating the cumene hydroperoxide at downstream of the oxidation tower, a disintegration tower for forming coarse acetone and coarse phenol by disintegrating the concentrated cumene hydroperoxide by the acid material at downstream of the concentration tower and each kinds of distillation tower for separating and refining the coarse phenol and the coarse acetone at downstream of the disintegration tower, which is provided with a hydrophilic contaminants removing assembly, comprising:

coalescing means provided with a fiber layer in which capillary tubes are formed and having characteristics of alkali resistance and solvent resistance, for coalescing and separating the moisture including the hydrophilic contaminants from the oil-state liquid;

liquid feeding means for supplying a mixed liquid consisting of the moisture including the hydrophilic contaminants and the oil-state liquid to the said coalescing means;

water collecting means for collecting the moisture including the hydrophilic contaminants which is coalesced and separated; and oil collecting means for collecting the oil-state liquid after the moisture including the hydrophilic contaminants is separated and removed therefrom, in at least one portion on the passage between the oxidation tower and the concentration tower, between the disintegration tower and the distillation tower, or on the passage provided for feeding back the excess cumene from the concentration tower to the upstream side of the oxidation tower.

5. The phenol producing apparatus according to claim 4, wherein said coalescing means consists of:

a porous cylindrical-shaped holding cylinder which is adapted to be connected and disconnected from the main body of the removing assembly;

a fiber layer wound around the outer peripheries of the holding cylinder to be held by the holding cylinder, so that a highly densified portion having high fiber density is formed at both end portions, as well as includes a carbon fiber; and end plates attached to both end surfaces of the fiber layer and provided with an endless ring-shaped thin protrusion which protrudes into the fiber layer as being cut into the highly densified portion.

6. A phenol producing apparatus including a reaction tower for forming cumene by benzene and propylene, an oxidation tower for forming a cumene hydroperoxide by oxidizing the cumene at downstream of the reaction tower, a concentration tower for concentrating the cumene hydroperoxide at downstream of the oxidation tower, a disintegration tower for forming coarse acetone and coarse phenol by disintegrating the concentrated cumene hydroperoxide by the acid material at downstream of the concentration tower and each kinds of distillation tower for separating and refining the coarse phenol and the coarse acetone at downstream of the disintegration tower, which is provided with a hydrophilic contaminants removing assembly comprising:

a chamber containing the mixed liquid, means for supplying the mixed liquid from the chamber to a coalescing means, coalescing means for coalescing and separating the moisture from the mixed liquid resulting in the oil-state liquid, the oil-state liquid and the moisture being released from the coalescing means into a separated liquid chamber, the moisture forming a water sedimentation layer at a bottom portion of the separated liquid chamber, means cooperating with the bottom portion of the separated liquid chamber for collecting the water sedimentation layer in at least one portion on the passage between the oxidation tower and the concentration tower, between the disintegration tower and the distillation tower, or on the passage provided for feeding back the excess cumene from the concentration tower to the upstream side of the oxidation tower; and means cooperating with an upper portion of the separated liquid chamber for collecting the oil-state liquid;

wherein the coalescing means comprises:

an alkali resistant and solvent resistant fiber layer including capillary tubes, a cylindrical shaped porous holding cylinder having end portions connectable and disconnectable from a main body of the removing apparatus, wherein the fiber layer is wound about the outer peripheries of the holding cylinder so as to be held by the cylinder, the fiber layer including a highly densified portion formed at the end portions, and end plates attached to both end portions and including an endless ring-shaped thin protrusion protruding toward and cutting into the highly densified portion of the fiber layer.

* * * * *

UNITED STATES PATENT AND TRADEMARK OFFICE
CERTIFICATE OF CORRECTION

PATENT NO. : 5,512,175
DATED : April 30, 1996
INVENTOR(S) : Mikio SATO ET AL

It is certified that error appears in the above-indentified patent and that said Letters Patent is hereby corrected as shown below:

On the title page, the line after item [19] should read as follows:

--Sato et al.--

Also, item [75] should read as follows:

-- [75] Inventors: Mikio Sato, Sagamihara; Tsuneo Yamaguchi, Kawasaki, both of Japan--

Signed and Sealed this

Thirtieth Day of July, 1996

Attest:

BRUCE LEHMAN

*Attesting Officer*  *Commissioner of Patents and Trademarks*